United States Patent [19]

Barrington

[11] 4,151,841
[45] May 1, 1979

[54] IMPLANTABLE PENILE PROSTHESIS
[75] Inventor: James E. Barrington, Woburn, Mass.
[73] Assignee: Abcor, Inc., Wilmington, Mass.
[21] Appl. No.: 912,325
[22] Filed: Jun. 5, 1978

Related U.S. Application Data
[63] Continuation-in-part of Ser. No. 872,915, Jan. 27, 1978.
[51] Int. Cl.² .................................................. A61F 5/00
[52] U.S. Cl. ....................................................... 128/79
[58] Field of Search .................................. 128/79; 3/1

[56] References Cited
U.S. PATENT DOCUMENTS

| 3,893,456 | 7/1975 | Small et al. | 128/79 |
| 3,987,789 | 10/1926 | Timm et al. | 128/79 |
| 4,066,073 | 1/1978 | Finney et al. | 128/79 |

*Primary Examiner*—Lawrence W. Trapp
*Attorney, Agent, or Firm*—Richard P. Crowley

[57] ABSTRACT

A penile prosthesis adapted for surgical implantation in the penis for the treatment of erectile impotence is provided, which penile prothesis comprises a bundle of parallel flexible, plastic, rod-like elements which, due to internal surface friction between the individual rod elements, resist flexure, the rod elements tightly wrapped in a flexible sheath element, each end of the rod elements having a plastic cap means to protect the prosthesis from damage by the bundled plastic rod elements and a flexible medically acceptable material which sheaths the rod elements to seal out body fluids and tissue, whereby on implantation an erect or flaccid penile posture can be obtained at will.

10 Claims, 1 Drawing Figure

U.S. Patent     May 1, 1979     4,151,841
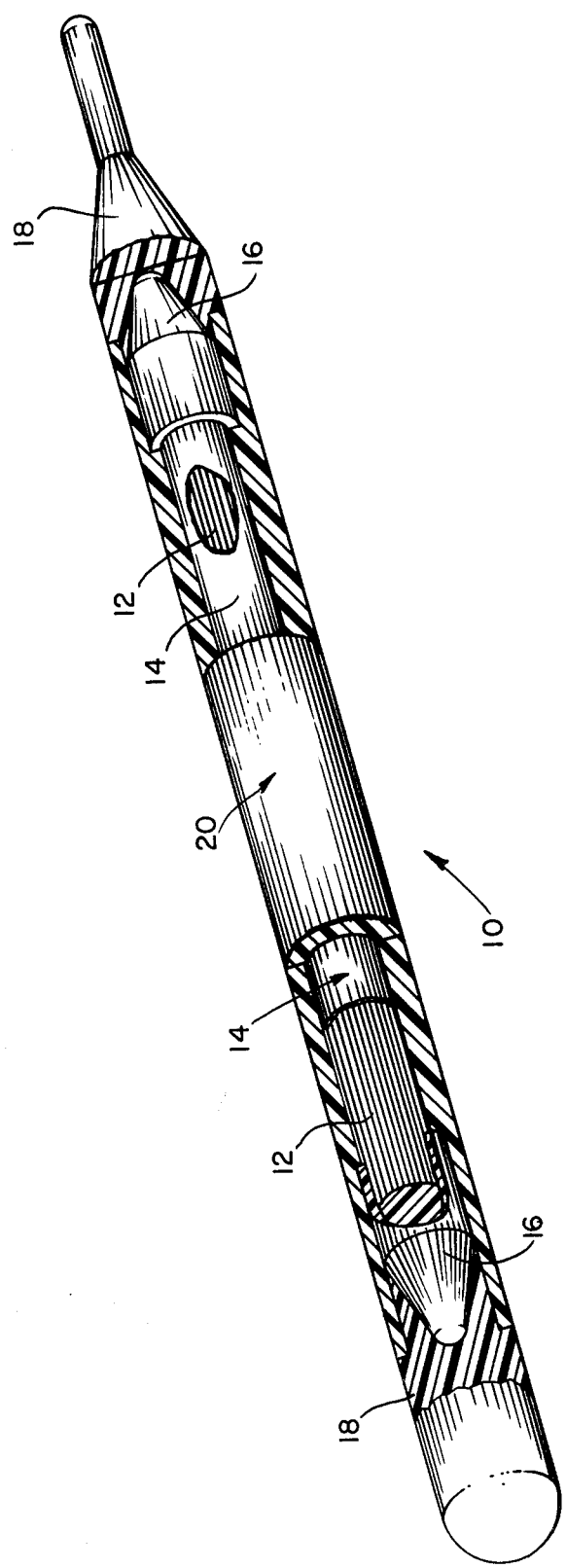

IMPLANTABLE PENILE PROSTHESIS

REFERENCE TO PRIOR APPLICATIONS

This application is a continuation-in-part of my U.S. Pat. application Ser. No. 872,915 filed Jan. 27, 1978, hereby incorporated by reference in its entirety.

BACKGROUND OF THE INVENTION

1. Field of the Invention

This invention relates to a mechanical penile prosthesis, to its manner of construction, and its use for the treatment of erectile impotence or as a functional component of a penile-replacement prosthesis.

2. Description of The Prior Art

Impotency is not only psychologically based, but can be related to nerve or vascular damage that may have been caused by severe diabetes, multiple sclerosis, spinal-cord injury or surgery in the lower abdomen, such as removal of the bladder or for rectal cancer, or it can also be the result of advanced age, trauma, and the side effects of drugs.

One surgical treatment for impotence involves, in particular, impotence caused by circulatory ills and revascularization (see *Medical World News*, Jan. 10, 1977, pp. 25-27 "Controversy over Penile Implants for Impotence"). While this technique has been proven to be simple and apparently quite successful, it is limited to impotence that is caused by circulatory problems. Accordingly, it cannot be used to help patients with psychogenic or neurogenic impotence.

Another procedure that is being adopted by surgeons for erectile impotence is the use of a penile prosthesis. This treatment is being used not only for impotence caused by age, disease, radical surgery, etc., but is also being used for psychogenic erectile impotence, but only after careful patient evaluation, generally when conventional sex therapy fails.

The modern era of penile implants is but five years old, spawned by development of two new, though very different, prostheses. One emphasizes simplicity, both of surgery and function, but gives the recipient a permanent erection. The other offers the patient a choice of flaccidity or erection, but is costlier, more complex and more prone to mechanical problems.

A simpler prosthesis has been developed (*Medical World News* (supra)) which consists of a rod-like device with a silicone-sponge interior encased in a medical-grade silicone exterior. It is implanted in pairs within the crura and the corpora cavernosa.

A more sophisticated prosthesis comprises a totally implantable device using paired, inflatable, silicone cylinders within the corpora cavernosa connected to a hydraulic pumping device implanted in the patient's scrotum. The fluid reservoir for pumping pressure is placed behind the patient's rectus muscle.

In the impotent patient, the flow of blood to the penis' blood vessels is impaired. The increased flow is necessary for the tissue surrounding the vessels to expand and cause erection. A prosthesis, or artificial device, that causes erection is surgically inserted into the cavities of spongy tissue in the penis. It is these two cavities that normally fill with blood during erection.

With the inflatable device an inert fluid takes the place of the blood supply. Two inflatable silicone tubes are inserted along the side of the penis' spongy tissue. The cylinders are attached by small tubes leading to a fluid-filled sac which is implanted under the patient's lower abdominal muscles. By manipulating the small valves placed under the skin of the scrotum, the patient may fill or empty the penile cylinders with fluid, thus causing erection, also called tumescence, or detumescence.

The big advantage of the inflatable device over the permanently hard silicone rods is aesthetic in that the patient does not have a permanent erection, but insertion of the device requires a more major operation and there are more postoperative complications. The surgical insertion of an inflatable prosthesis, moreover, generally precludes the ability to have a normal unaided erection, although this is not usually true with the non-inflatable device.

SUMMARY OF THE INVENTION

My invention relates to a simple, mechanical, implantable, penile prosthesis designed to be implanted surgically in the penis for the treatment of erectile impotence or as a functional component of a penile-replacement prosthesis. In particular my invention relates to a mechanical penile prosthesis which comprises a plurality of flexible elements therein, which individual elements due to the internal surface friction resist flexure, whereby the internal friction between the individual elements may be overridden manually and the penile prosthesis containing such elements bent to another and different configuration, so that the penile prosthesis when implanted provides for the erect or flaccid penile posture of the patient at will.

My penile prosthesis when implanted is longitudinally incompressible and resists lateral flexure which permits the user/patient to place an otherwise flaccid penis in position to engage in successful copulation. The flaccid posture of the prosthesis allows the patient's penis to rest in a manner that imitates the natural flaccid posture of the penis. The penile prosthesis, hermetically sealed within a medically acceptable sheath element, typically is implanted in pairs in a manner such as, for example, set forth in U.S. Pat. No. 4,066,073 issued Jan. 3, 1978, hereby incorporated by reference.

In the preferred embodiment my mechanical penile prosthesis comprises an outer elongated flexible sheath element which surrounds and seals a plurality of individual elements within the sheath element, which individual elements, due to the internal surface friction between such elements, resist flexure and provide for internal friction, so that the sheath containing such elements may be bent to various configurations between a flaccid state and an erect state when implanted in the penis. The internal friction is sufficient so that, on manual overriding by the user or patient of the internal friction of the individual elements in the sheath, the penile prosthesis maintains its shape until it is again bent or straightened as desired. Typically the elements are sealed with a medically acceptable material into an elongated fashion, such as by the employment of a medically acceptable silicone or similar functioning flexible, sterilizable, polymeric material, with the outer polymeric material adapted to seal out body fluids and tissues from the individual elements of the penile prosthesis.

The rod elements may be of varying materials and have varying rod diameters, while rod length typically ranges from about 4 to 12 centimeters. In the selection of rod diameters and material of construction, the flexure of the bundle of rod elements; i.e., the rod elements resistant to bending, is balanced against the internal friction of the rod elements in the bundle. The friction of the rod elements in the rod bundle is based on the diameter and length of the rod; i.e., the surface area, and the tangential contact between the rods and the nature of the rod material which, in toto, provides for the frictional component. The friction of the bundle of rod elements should be greater; e.g., slightly greater in the preferred embodiment of the selected rod length and diameter, than the flexural resistance of all the rods, so that easy manual movement of the penis permits a flaccid or erect penile posture.

Typical end cap means are employed at each end of the rod bundle to help maintain the rod in the bundle within the sheath, to permit limited movement of the rod and to protect the polymeric encasement material of the prosthesis from damage by the rod ends. For example, a rod bundle may be composed of rod elements of a flexible polycarbonate polymer having a rod diameter of about 0.5 to 2.0 millimeters, and a length of about 4 to 12 centimeters, with the rod bundle having about 150 to 250; e.g., 197 to 204, 0.5 millimeter rod elements for a bundle diameter of about 0.6 to 1.0; e.g., 0.8, centimeters with end caps of a plastic material, such as polycarbonate, which is compatible and may be bonded integrally to the encasement polymer of silicone rubber.

The friction between rod elements may be controlled, such as increased by imparting a texture such as annular ridges or surface corrugations to the surface of the rods or by the application and use of chemical treatment to roughen the rod surface or by a coating; e.g., a polymeric coating, on the rod element. The internal friction of the rod bundle may therefore be controlled more independently of the coefficient of friction inherent in the material of the rods.

In the most preferred embodiment my penile prosthesis comprises an outer elongated flexible sheath element; a plurality of elongated, generally parallel, contacting, flexible, rod elements typically formed of a semirigid, flexible, plastic material, the rod elements enclosed within the flexible sheath element and the internal friction between the rod elements sufficient to resist flexure and to permit the elements to be bent to desired configuration; and means to enclose the rod elements at each end of the sheath element, such as by the employment of a plastic cap or other means, to protect the semirigid rubber ends of the penile prosthesis from damage by the bundles of rod element ends and outer flexible sheath element, such as of a flexible medically acceptable polymer such as a heat-sterilizable silicone rubber tube, which is integral with the semirigid ends at each end of the rod elements, such as of the silicone rubber end elements, to sheath completely the rod-element-bundle assembly and to seal out body fluids and tissues.

BRIEF DESCRIPTION OF THE DRAWING

The drawing illustrates a partially cutaway perspective sectional view of my elongated mechanical penile prosthesis.

DETAILED DESCRIPTION OF THE EMBODIMENT OF THE INVENTION

The drawing illustrates my penile prosthesis 10 containing a plurality of bundles of elongated, generally parallel arranged, flexible, plastic rod elements 12, which rod elements are tightly wrapped in a flexible sheath element 14, the rod elements resisting flexure because of internal tangential surface friction between the tightly packed rod elements in the bundles; however, the internal tangential surface friction may be overcome manually and the flexible rod elements may be bent sufficiently to assume the shape of a flaccid penis or an erect penis. At each end of the plurality of bundle rod elements 12 there is a plastic cap 16, each end of the rod bundle elements fitting within the plastic cap. At each end of the penile prosthesis is a semirigid end typically composed of a silicone rubber or other medically accepted polymer 18, with a plastic cap 16 protecting the silicone rubber ends 18 from internal damage by the rod elements 12. The enclosing tube element, which is composed of a flexible silicone rubber polymer 20, is formed integrally with the ends 18 to sheath completely the rod-bundle-element assembly to form the penile prosthesis, and which flexible silicone rubber tube element 20 seals out body fluids and tissues. The narrow tapered end of the penile prosthesis is the proximal portion of the implant which is receivable in crura of the corpus cavernosum for supporting the implant, with the opposite end of the penile prosthesis 10 forming the mouth of the stiff distal portion suitable for positioning in the pendulous penis.

My penile prosthesis may assume various forms and be provided of and formed of material of different compositions; however, the rod elements may be formed generally of a flexile, semistiff, polymeric material, such as, for example, nylon or polycarbonate polymer, and may range in varying diameter, depending upon the degree of internal friction desired and the amount of manual force required to override the internal friction to place the penis in this desired position. The rod elements are encased in the sheath 14 employing a suitable flexible plastic material, such as, for example, a plastic tube composed of silicone rubber. The plastic cap elements at each end of the tube and sheath are designed to form an integrally unitary penile prosthesis and may be of the same or different plastic material, including, for example, but not limited to, medically acceptable polymeric materials, such as polycarbonate resins, polysulfone resins, polyacetyl resins, silicone rubber or similar materials.

In operation and after implantation the penis is simply bent to the desired position by overcoming the internal friction of the rod elements in the penile prosthesis. Therefore an erection is produced by bending the penis up to the erect position and conversely a flaccid penis is produced by manually bending the penis down to the flaccid position.

It is understood that the invention has been described in its specific embodiments and that various changes and modifications may be made thereto by those persons skilled in the art without departing from the spirit and scope of my invention and the illustration thereof.

What I claim is:

1. A penile prosthesis adapted for surgical implantation in the penis for the treatment of erectile impotence, which penile prosthesis comprises:
    (a) a plurality of elongated, generally parallel, flexible, rod elements, the rod elements bundled together to be in a contacting relation and resistant to flexure due to the internal friction between the bundled individual rod elements;
    (b) an outer elongated element adapted to surround and contain said plurality of rod elements and to seal the interior of the rod elements from body fluids and tissues; and (c) the prosthesis at the proximal end adapted to be receivable in the crura of the corpus cavernosum for supporting the penile prosthesis when implanted, whereby on implantation the penis may be moved from a flaccid penile position to an erect penile position through a manual overcoming of the internal friction to flexure produced by the rod-like elements within the penile prosthesis.

2. The penile prosthesis of claim 1 which includes a cap-like element positioned over each end of the bundle of rod elements in the penile prosthesis.

3. The penile prosthesis of claim 1 wherein the rod elements are composed of a flexible polymeric material.

4. The penile prosthesis of claim 3 wherein the polymeric material comprises a polycarbonate or polyamide polymer, or acrylic, or polyvinyl polymer.

5. The penile prosthesis of claim 1 wherein the outer element is composed of a medically accepted sterilizable polymeric material.

6. The penile prosthesis of claim 1 wherein the rod elements have a length of from about 4 to 12 centimeters and a diameter of about 0.5 to 2.0 millimeters, with about 150 to 250 rod elements in the bundle of rod elements.

7. The penile prosthesis of claim 1 wherein the rod elements are characterized by a surface means to change the friction between the rod elements.

8. The penile prosthesis of claim 7 wherein the rod elements are characterized by a surface texture to increase the friction between the rod elements.

9. A penile prosthesis adapted for the surgical implantation in the penis for the treatment of erectile impotence, which penile prosthesis comprises:
  (a) a plurality of elongated, generally parallel, flexible, plastic rod elements bundled together in a contacting relationship and resistant to flexure due to internal surface friction between the individual rod-like elements in the bundle formed by the plurality of elements;
  (b) a flexible plastic sheath element enclosing the bundle of rod elements;
  (c) plastic end cap elements over each end of the bundle of rod elements;
  (d) the plastic end elements form the proximal and distal ends of the penile prosthesis; and
  (e) an outer, medically acceptable, polymeric tube surrounding the rod elements and integral with the end elements to sheath completely the rod-like bundle to seal out body fluids and tissues, whereby the penile prosthesis when implanted permits movement by manually overcoming the internal surface friction of the rod elements from a flaccid position.

10. The penile prosthesis of claim 9 wherein the rod elements have a length of from about 4 to 12 centimeters and a diameter of about 0.5 to 2.0 millimeters, with about 150 to 250 rod elements in the bundle of rod elements.

* * * * *